United States Patent
Maad

(10) Patent No.: US 8,235,530 B2
(45) Date of Patent: Aug. 7, 2012

(54) OBJECT POSITIONING WITH VISUAL FEEDBACK

(75) Inventor: Kristofer Maad, Knivsta (SE)

(73) Assignee: C-Rad Positioning AB, Uppsala (SE)

( * ) Notice: Subject to any disclaimer, the term of this patent is extended or adjusted under 35 U.S.C. 154(b) by 421 days.

(21) Appl. No.: 12/632,526

(22) Filed: Dec. 7, 2009

(65) Prior Publication Data

US 2011/0135190 A1 Jun. 9, 2011

(51) Int. Cl.
*G03B 21/26* (2006.01)
(52) U.S. Cl. .......................... 353/28; 250/492.1; 600/595
(58) Field of Classification Search .................... 353/28; 250/492.1; 600/595
See application file for complete search history.

(56) References Cited

U.S. PATENT DOCUMENTS

| | | | |
|---|---|---|---|
| 5,820,553 A | 10/1998 | Hughes | |
| 6,516,046 B1 | 2/2003 | Fröhlich et al. | |
| 6,690,964 B2 | 2/2004 | Bieger et al. | |
| 2002/0002330 A1 | 1/2002 | Vilsmeier | |
| 2002/0023652 A1 | 2/2002 | Riaziat et al. | |
| 2002/0065461 A1 | 5/2002 | Cosman | |
| 2003/0225325 A1 | 12/2003 | Kagermeier et al. | |
| 2004/0002641 A1 | 1/2004 | Sjogren et al. | |
| 2005/0195587 A1 | 9/2005 | Moctezuma De La Barrera et al. | |
| 2005/0265516 A1 | 12/2005 | Haider | |
| 2005/0283068 A1 | 12/2005 | Zuccolotto et al. | |
| 2006/0079757 A1 | 4/2006 | Smith et al. | |
| 2006/0264737 A1 | 11/2006 | Faber et al. | |
| 2007/0253614 A1 | 11/2007 | Jung et al. | |

FOREIGN PATENT DOCUMENTS

WO   WO 2009/011643 A1   1/2009
WO   WO-2009/043118 A1   4/2009

*Primary Examiner* — Seung C Sohn
(74) *Attorney, Agent, or Firm* — Birch, Stewart, Kolasch & Birch, LLP

(57) ABSTRACT

A positioning system comprises a pattern projector (70) for projecting a 2D/3D pattern (45) onto an object surface. The 2D/3D pattern (45) is detected by a detector (80, 85), which generates a detection signal that is employed by a pattern analyzing circuit (110) for generating a surface representation of the object surface. A correction analyzing circuit (130) generates a correction signal representative of a discrepancy in position and/or posture of the surface representation relative a stored reference surface representation. The correction signal is employed to generate information (55, 56) that is projected by a light projector (70, 75) onto the object surface. The projected information (55, 56) is indicative of the determined discrepancy in object position and/or posture.

25 Claims, 9 Drawing Sheets

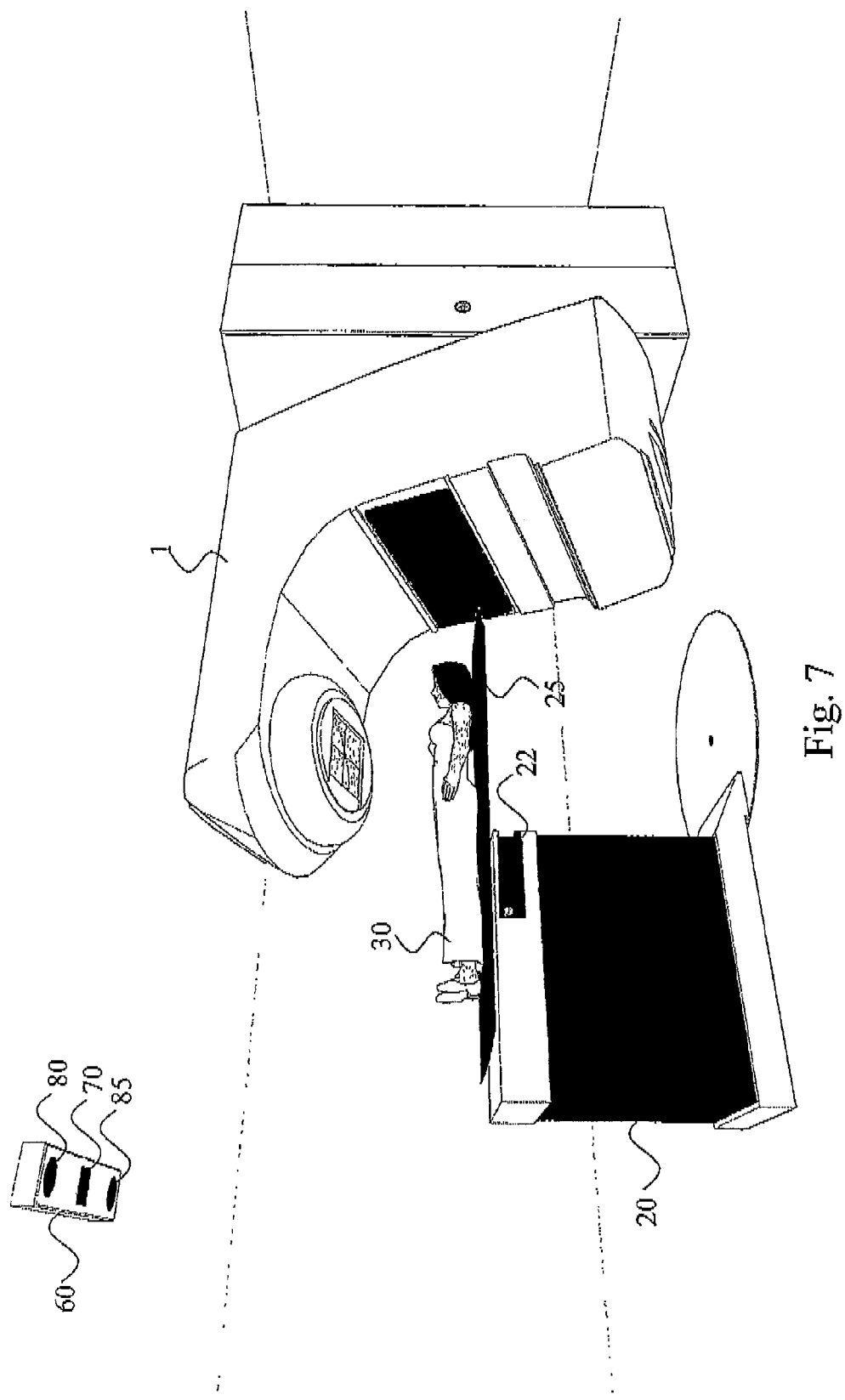

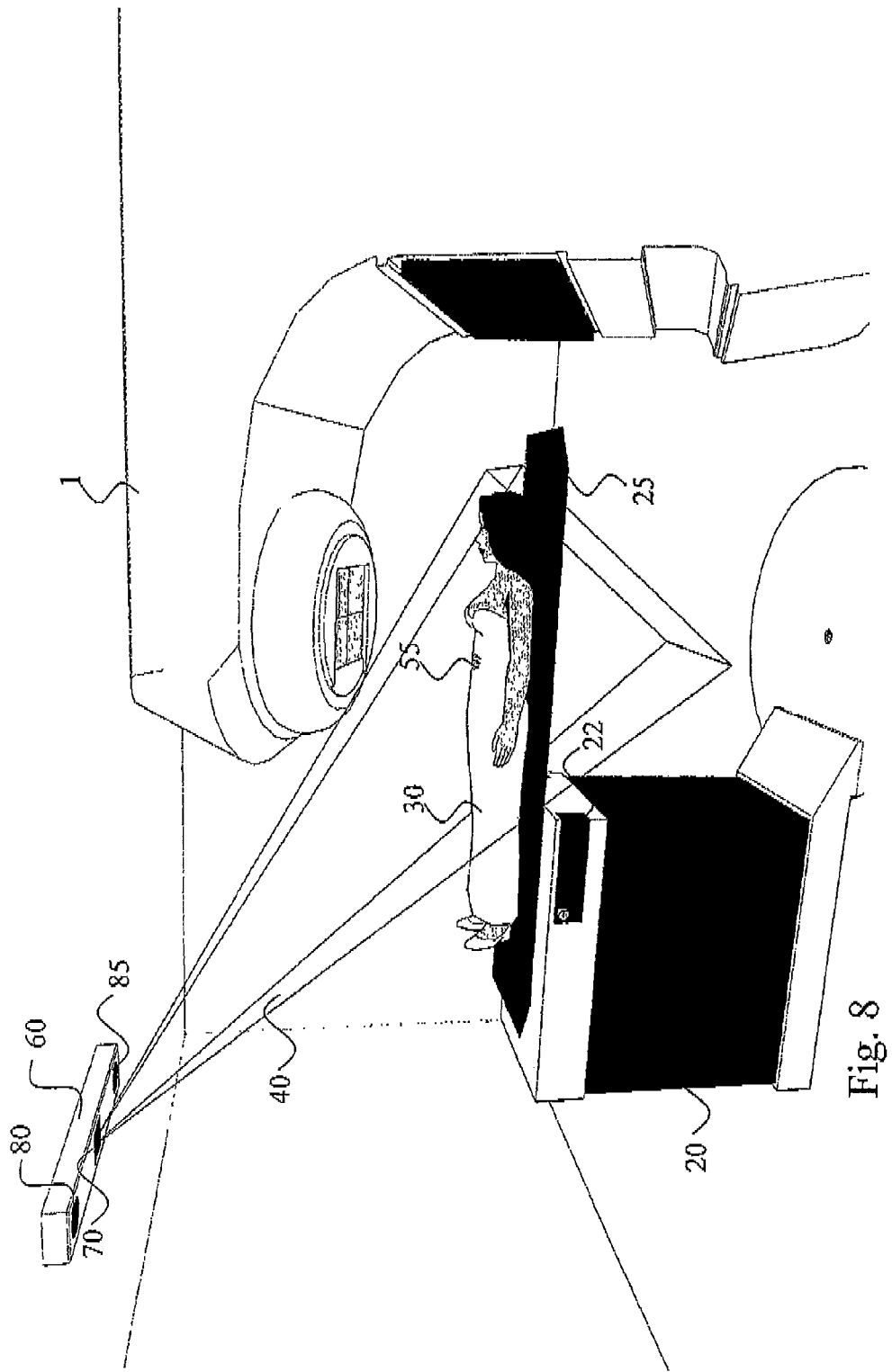

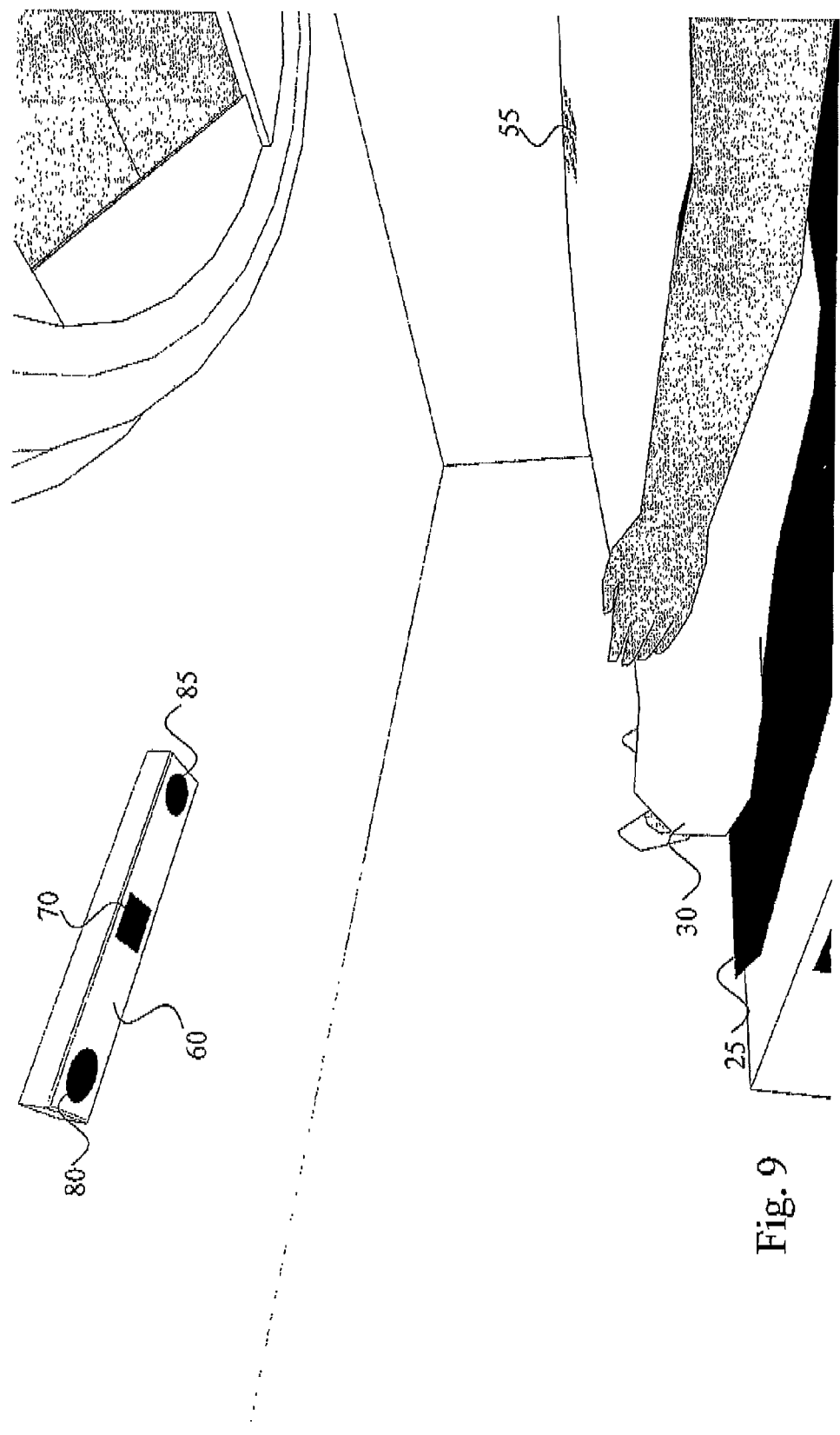

OBJECT POSITIONING WITH VISUAL FEEDBACK

TECHNICAL FIELD

The present invention generally relates to accurate positioning of an object, and in particular to a system and method for achieving visual feedback regarding the object positioning.

BACKGROUND

During the past decades there have been considerable developments within the fields of radiation therapy and medical diagnosis. The performance of external beam radiation therapy accelerators, brachytherapy and other specialized radiation therapy equipment has improved rapidly. Developments taking place in the quality and adaptability of radiation beams have included new targets and filters, improved accelerators, increased flexibility in beam-shaping through new applicators, collimator and scanning systems and beam compensation techniques, and improved dosimetric and geometric treatment verification methods have been introduced.

Furthermore, a number of powerful 3-dimensional diagnostic techniques have been developed, ranging from computed tomography (CT), positron and single photon emission computed tomography (PET and SPECT) to ultrasound and magnetic resonance imaging and spectroscopy (MRI and MRS). Equally important is the increased knowledge of the biological effect of fractionated uniform and non-uniform dose delivery to tumors and normal tissues and new assay techniques, including the determination of effective cell doubling times and individual tissue sensitivities, allowing optimization of the dose delivery to tumors of complex shape and advanced stages.

A major problem in the field of radiation therapy and diagnosis today is the accurate positioning of a patient on a patient couch prior radiation therapy or diagnosis in order to achieve correct position of patient body parts to be treated or diagnosed.

US 2005/0283068 discloses a motion tracker for a MRI system. A structure comprising infrared (IR) reflectors is mechanically attached to the patient body. An IR scanner projects IR light onto the IR reflectors and a camera is arranged for monitoring the motion of the IR reflectors in real time. Feedback information in up to six dimensions can be obtained both before and during MRI scanning. The feedback information is displayed on a display screen for the patient or medical personnel trying to reposition the patient based on the feedback information.

A disadvantage of the system of US 2005/0283068 and similar patient positioning systems of the prior art is that the feedback information defining how the patient body should be repositioned is displayed on a display screen. This display screen generally has to be arranged a distance away from the radiation system to allow the gantry sufficient space to rotate safely around the patient without any risk of hitting the display screen. However, such a remote arrangement of the display screen in relation to the couch onto which the patient is lying makes it cumbersome for the medical personnel standing next to the couch and patient to correctly reposition the patient while simultaneously looking at the remote display screen.

SUMMARY

Embodiments as disclosed herein solve this and other problems of the prior art arrangements.

It is a general objective to provide a positioning system and method displaying repositioning feedback information in the vicinity of the area where the personnel is operating.

It is a particular objective to provide a positioning system and method projecting the repositioning feedback information onto a surface in connection with the couch.

These and other objectives are met by embodiments as disclosed herein.

Briefly, a positioning system comprises a pattern projector configured to project a two-dimensional 2D or three-dimensional (3D) pattern onto a surface of an object, such as patient, positioned on a couch. At least one detector or camera responsive to the projected 2D/3D pattern generates a detection signal representative of the detected 2D/3D pattern on the object surface. The detection signal is processed by a pattern analyzing circuit that is configured to generate a surface representation of at least a portion of the object surface based on the detection signal. A correction analyzing circuit compares the generated surface representation with a stored reference surface representation in order to generate a correction signal. The correction signal is representative of a discrepancy in position and/or posture of the surface representation relative the reference surface representation. The correction signal is further employed to generate information representing the position and/or posture discrepancy. The information is projected by a light projector onto the object surface or onto another surface of the couch.

There the projected information is directly available for the personnel that are repositioning the object to reach a target position and posture as defined by the reference surface representation. No remote display screens that can collide with any rotating parts of a nearby machine, such as radiation gantry, surgical or assembling robotic arm, etc., are thereby needed in order to visually convey information required by the personnel to determine the necessary object repositions to reach the target position and/or posture.

An aspect relates to an object positioning method and involves projecting a 2D/3D pattern onto a surface of an object positioned on a couch. A detection signal representative of the detected 2D/3D pattern on the object surface is generated and employed for generating a surface representation of the object surface. The surface representation is compared to a reference representation in order to generate a correction signal representative of a discrepancy in object position/posture relative a target position/posture as concluded based on the comparison. The correction signal is employed to generate information that is projected onto the object surface to thereby visually convey information defining this discrepancy in position and/or posture.

BRIEF DESCRIPTION OF THE DRAWINGS

The invention, together with further objects and advantages thereof, may best be understood by making reference to the following description taken together with the accompanying drawings, in which:

FIG. 7 is a schematic overview of a radiation gantry equipped with a positioning system according to another embodiment;

FIG. 8 is a schematic overview of the radiation gantry of FIG. 7 during operation;

FIG. 9 is a view of the projecting and detecting arrangement employed in connection with the radiation gantry of FIGS. 7 and 8;

DETAILED DESCRIPTION

Figure 1:
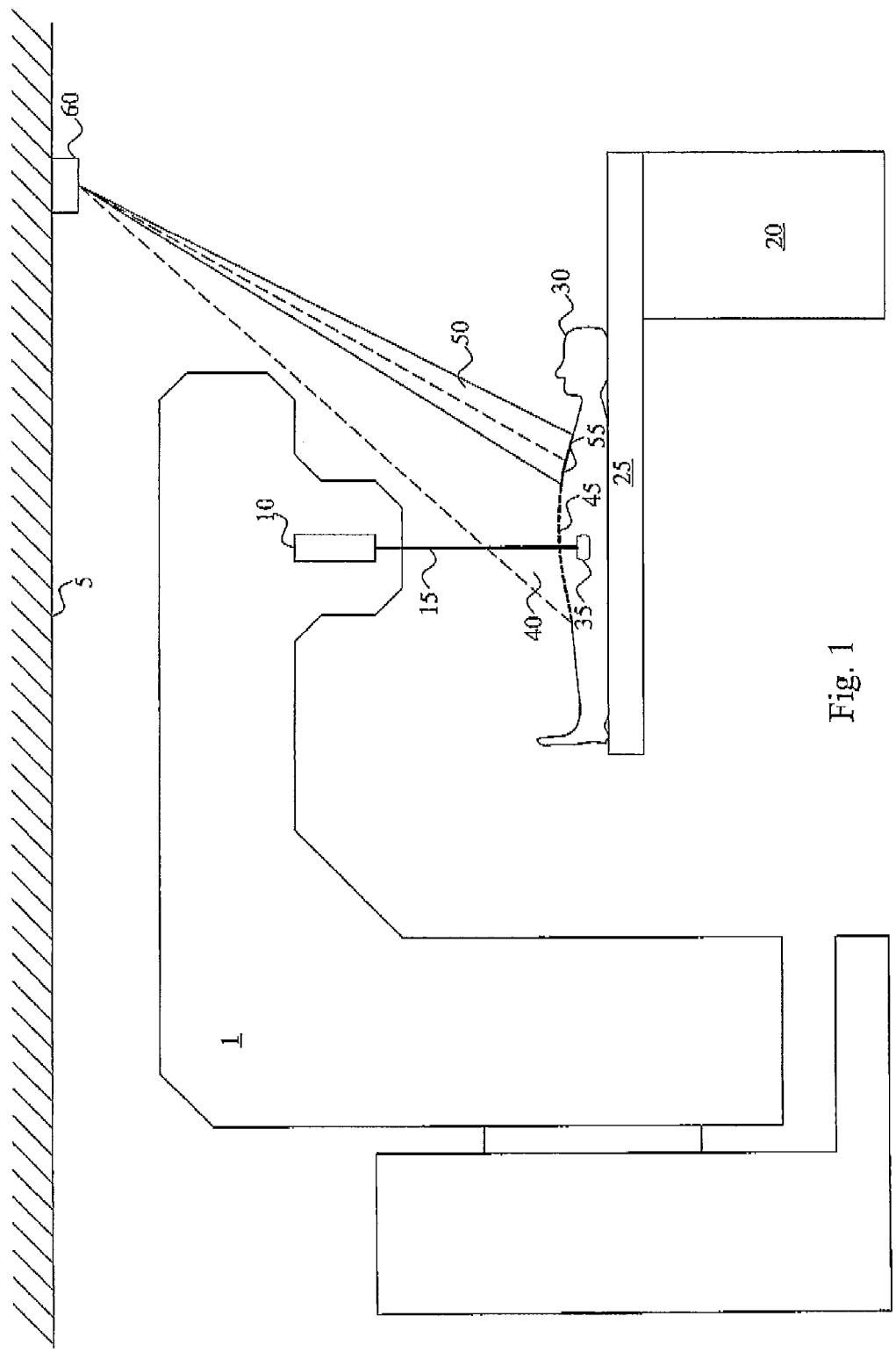
FIG. 1 is a schematic overview of a radiation gantry equipped with a positioning system according to an embodiment.

Throughout the drawings, the same reference numbers are used for similar or corresponding elements.

The embodiments generally relate to a non-contact method and system for determining a position of an object and projecting visual information indicative of a discrepancy of the determined position and a target position.

The embodiments are advantageously employed within the medical field and in particular when positioning a patient, such as an animal patient in veterinary applications or a human patient, on a couch for the purpose of conducting diagnostic imaging, radiation therapy or robotic surgery on the patient. In those applications it is crucial for achieving an effective diagnosis or treatment that the patient is correctly positioned on the couch. Not only animal or human patients benefit from accurate positioning in these applications. It is common practice to arrange different objects close to the patients on the couch. For instance, fixation equipment can be present on the couch for the purpose of fixing the patient in a given posture. Example of such fixation equipment include cushions, including inflatable cushions, support structures etc. Generally these devices should be placed and positioned correctly before the patient is placed on the couch.

As is well known in the art, in these medical applications the position of the patient and optionally of the fixation equipment is determined relative a defined coordinate system. The patient/equipment position as determined in the coordinate system can then be compared to a corresponding reference position in the coordinate system to determine any discrepancy that requires a reposition of the patient or equipment.

For a better understanding of the need for correct positioning, it may be useful to start with a brief introduction of a radiation therapy process.

Generally, the first step in a radiation therapy process is performing a diagnostic process or diagnosing. Different diagnostic machines are employed to localize a tumor and adjacent tissues and organs. This diagnostic anatomical information is used to as accurately as possible pinpoint the exact location of the tumor in the patient and detect any organs or tissues that may be affected or should be avoided by the radiation beam in the subsequent radiation therapy treatment. It is normally advisable to use anatomical information from different diagnostic machines, since different imaging techniques give different anatomical information. For an example, CT is superior for obtaining density information and MRI for retrieving anatomical information about soft tissues near bony structures, such as the central nervous system. Therefore, information from different diagnostic machines complement each other and should together give a sufficient picture of the target volume and surrounding tissues. The diagnostic information collected in the diagnostic machine(s) is generally defined in relation to a coordinate system. If multiple different diagnostic machines are used, it is important to have a common coordinate system in which the diagnostic and anatomical information from the different diagnostic machines can be defined. Therefore the patient position is determined in connection with each of the medical machines and a known transformation between the coordinate system of the diagnostic machine and the coordinate system of the positioning system can be used to define the diagnostic information in the coordinate system of the positioning system, which is then employed as the common coordinate system. Alternatively, a first transform of the coordinates of the diagnostic information from the machine coordinate system to the common coordinate system is used and a second transform of the coordinates of the patient from the couch coordinate system to the common coordinate system. In either case, the diagnostic information can be co-expressed in the same coordinate system as the positioning information.

In subsequent diagnostic machines, the position and posture of the patient is preferably determined by the positioning system and compared to the corresponding reference position and posture of the patient, such as determined in connection with another diagnostic machine. Embodiments as disclosed herein can be employed for the accurate positioning of the patient in these cases. Based on the measured anatomical information, a treatment or dose planning process is carried out. In the treatment planning the goals are generally to:

Achieve the desired dose in the target volume;
Uniformly distribute the dose in the target volume;
Avoid high doses in surrounding tissues and organs and in organs at risk; and
Limit the total dose received by the patient.

In order to achieve these goals, the measured anatomical information is investigated to define the target volume and identify organs at risk. Thereafter, dose prescription for the target volume and tolerance level of organs at risk is specified. Further, radiation modality and treatment technique are selected for the particular treatment. Having decided treatment technique the number of beam portals (sources) and the directions of the incidence of the beams are selected and optimized, considering the present anatomical information. Also beam collimation, beam intensity profiles, fractionation schedule, etc. are selected and optimized based on the actual patient information. Once these parameters are optimized, a dose distribution in the patient is calculated and, if it fulfils the general goals, a treatment or dose plan is composed.

The treatment plan should include all relevant information for the actual radiation therapy treatment, such as the selected and optimized parameters from the treatment planning and the present set-up of the radiation therapy machine and its settings. Before the actual radiation therapy treatment an optional treatment simulation may be performed to test and verify the treatment plan. In the simulation procedure, the settings and equipment according to the treatment plan are used. Often portal images, i.e. images based on the treatment beam itself, are used to verify the treatment and monitor its reproducibility. Furthermore, e.g. in vivo dosimetry or related techniques may be used to check the delivered radiation dose in the target volume and/or in adjacent tissues, preferably in organs at risk. If the measured data corresponds to the calculated data in the treatment plan, the actual radiation therapy treatment may be initiated. However, if some divergence between the measured and calculated data is detected and the divergence exceeds a safety threshold, a change in the treatment plan must be performed. This change may in some cases simply be a resetting of parameters but also a larger change in the treatment plan, such as completing the treatment planning process with more anatomical information from a new diagnostic measurement. Either way, a new treatment plan is determined, which may be tested and verified in an optional new treatment simulation.

A radiation therapy treatment is then performed with the equipment, set-up and settings specified in the treatment plan. It is vitally important that the patient is positioned accurately, based on the treatment plan, in the radiation therapy machine. A misplacement of only a few millimeters may cause damages to adjacent tissues and organs and make the treatment ineffective. Embodiments as disclosed herein can advantageously be employed for positioning the patient according to a reference position defined in the treatment plan. Once the positioning is ready, the beams irradiate the patient according to the treatment plan to deliver the calculated dose in the target volume.

Although, the radiation therapy treatment in the section above has been described in relation to a single treatment occasion, the actual dose delivery is most often fractionated into several, often 20-30, fractions. This means that a total radiation therapy treatment usually extends over a period of days, weeks or in some occasions even months. This means that the problem of accurate patient positioning is present at each such radiation occasion. After each treatment occasion, a follow-up or treatment monitoring evaluates the hitherto performed radiation therapy, possibly leading to changes in the treatment plan before the next treatment fraction, similar to the simulation procedure discussed above.

In addition, different treatment machines may be employed. For example, at one treatment occasion a high-energy radiosurgery machine is used, whereas at the next occasion the treatment is performed with a radiation therapy machine adapted for curative radiation therapy. In this context, also medical machines not using curative, palliative or surgery radiation may be used. A typical example is different surgical equipment and appliances, where accurate patient positioning is required, such as equipment containing surgical robots.

According to the embodiments, a surface representation of the patient is preferably determined in connection with a medical machine in relation to a common overall coordinate system. For a diagnostic machine, this means that the representation is measured in connection with the measurements of the anatomical patient information. In a radiation therapy machine, including treatment simulation machines, the surface representation is measured before, during and/or after the actual dose delivery from the beam sources.

In the following, embodiments will be described in more detail with reference to the figures illustrating a positioning system arranged in connection with a radiation system employed for applying treatment radiation beams into a human patient. However, this should merely be seen as an illustrative example application. Generally, the positioning system can be used in any application where it is important to accurately position an object, such as human or animal patient, fixation equipment, etc., on a couch. This means that also in the manufacturing industries where robots are employed for joining different parts into an assembly can benefit from the positioning system as disclosed herein. In such a case, the couch onto which the object is positioned should be interpreted broadly to include any structure that carries the relevant object to be positioned correctly.

FIG. 1 is a schematic overview of a treatment room having a radiation therapy machine 1 with a radiation source 10 employed for directing radiation beams 15 into a target volume 35, such as cancerous tumor, of a patient 30 lying on a table top 25 of a couch 20. A positioning system is employed to determine and control the position of the patient 30 on the couch 20 to achieve an accurate and correct positioning of the target volume 35 relative the radiation beam 15 to meet the requirements of the previously determined treatment plan.

Figure 2:
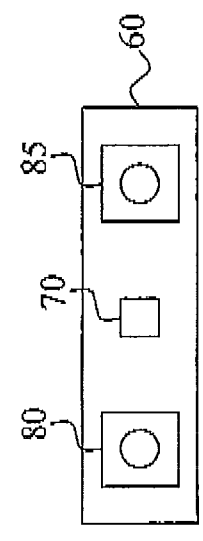
FIG. 2 illustrates an embodiment of projector and detectors of the positioning system.
Figure 3:
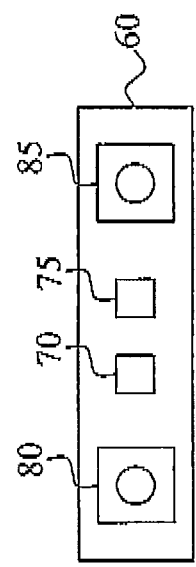
FIG. 3 illustrates another embodiment of projectors and detectors of the positioning system.

The positioning system comprises a pattern projector 70 more clearly seen in FIGS. 2 and 3. The pattern projector 70 is configured to project a 2- or 3-dimensional (2D or 3D) pattern 45 onto a surface of an object 30, here the patient 30 positioned on the couch 20. A detector 80 or multiple detectors 80, 85 of the positioning system is/are responsive to the projected 2D or 3D pattern 45. The at least one detector 80, 85 is further configured to generate a detection signal representative of the detected 2D or 3D pattern 45 on the surface of the patient 30.

Figure 4:
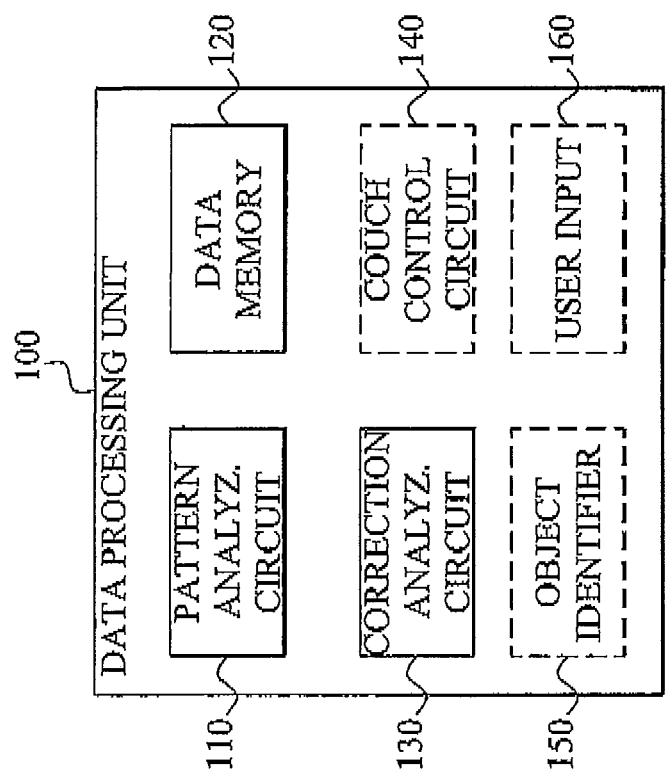
FIG. 4 is a schematic block diagram of a data processing unit of the positioning system.

The detection signal from the detector 80, 85 is forwarded to a pattern analyzing circuit 110 illustrated in FIG. 4. The pattern analyzing circuit 110 is configured to generate a surface representation, such as 2D or 3D surface representation, of at least a portion of the surface of the patient 30 based on the detection signal. Thus, the pattern analyzing circuit 110 is able to determine the coordinates of at least a portion of the surface of the patient 30 based on the 2D or 3D pattern projected onto the patient surface and detected by the detector (s) 80, 85. The coordinates of the relevant patient surface is preferably expressed in a coordinate system associated with the positioning system or can be transformed or mapped into corresponding coordinates in a common coordinate system. In such a case, the pattern analyzing circuit 110 preferably has access to the necessary coordinate transform, which has previously been determined and is stored in a connected data memory 120.

Determination of a surface representation based on detection of a projected 2D or 3D pattern onto a surface of an object is known in the art. Generally such surface representation can be divided into feature-based representations, point-based representations, model-based representations and representations based on global shape.

Briefly, the feature-based technique attempts to express surface morphology as a set of features which are extracted by a preprocessing step. Such features provide a compact description of the surface shape, though at the expense of losing information. Features used for surface registration generally fall into three categories: point features, curves and regions. Point features are salient, well-localized sparse loci of important geometric significance. The second type of features corresponds to contiguous lines or curves, consisting typically of differential structures such as ridges or boundaries between regions. Regions, in turn, are areas possessing some homogenous characteristic, such as consistent curvature sign.

Point-based techniques register surfaces on the basis of relatively dense point sets brought into correspondence, where these point sets constitute all, or a significant subset of the available surface point samples.

The mode-based technique involves expressing surface identification in one volume or surface tracking over a volume sequence, as a model which reconciles the likely shape and/or dynamic behavior of the surface according to some physically-based or surface evolution expression, with raw image data.

The above-mentioned feature-, point- and model-based techniques can be broadly described as relying on local information to register surfaces. Global shape based techniques in clear contrast register surfaces on the basis of global surface geometry. Examples of such techniques include spin-map representation and the eigenshape or appearance-based methods.

*Medical Image Analysis, September* 2000, 4(3): 201-217 provides a review of different surface registration techniques that can be used for generating a surface representation according to the embodiments. The teachings of this Medical Image Analysis article in terms of disclosing how a surface representation can be determined as briefly mentioned above is hereby fully incorporated by reference.

In the case of a 2D pattern, a single contour line 45 somewhere on the body of the patient 30 can be used. Due to the changing contour of the body when going in a longitudinal direction from one end to the opposite end, it is possible to measure a unique contour line almost everywhere over the body surface. However, to get a more accurate representation, a 3D pattern 45 may instead be used. In such a case, the 3D pattern can be projected onto the whole body surface or a suitable selected portion thereof, where a larger surface often implies a more accurate surface representation. The generated surface representation may be a continuous 3D surface of a portion of the body or several dispersed surfaces, the relative spatial relationship of which is known. Preferred dispersed surfaces coincidence with some of the standard anatomical reference points used in radiation therapy. These points have only very little tissue over the underlying skeleton and are therefore rather stable even if the skin is stretched. The standard reference points comprise e.g. upper and distal edges of ilium, upper point of symphysis pubis, distal point of scapula, upper point of nose, upper and lower point of patella and lower point of fibula. However, the 2D or 3D surface representation may be generated for any suitable portion of the patient's body, and especially in close connection with the tumor, e.g. by measuring the body portion contour directly above the tumor position.

Examples of pattern projecting techniques include photon-based techniques. For instance, a pattern projector 70 in the form of a laser scanning device sends out a sheet of laser light hitting a surface of the patient 30. A bright line 45 on the body is reflected and detected by the detector 80, 85. The detected image of the bright line is used to reconstruct the body contour. Every lit pixel in the image corresponds to a known vector. A point where this vector crosses the surface defined by the laser light is a known point on the surface of the body. If the scanning procedure stops now, a 2D surface representation of the patient 30 is obtained. However, if a 3D surface representation is required several such contour images can be used, since each image gives only a single contour. If the laser source is translated and/or rotated slightly between each image detection the detector 80, 85 will capture a series of successive contours.

This laser scanning technique is generally known as a triangulation technique and its accuracy depends on a number of factors, including resolution of the detector, accuracy of the laser sweeping mechanism, distance between the scanning device and the detector, calibration of the scanning device and the detector with reference to the common coordinate system, width of the laser line and angle at which the laser hits the surface of the body. These parameters are preferably selected and/or optimized before the actual measurements.

Suitable laser scanners applicable are commercially available for example from Latronix AB of Sweden. Examples of detectors that can be used in the triangulation laser scanning above, may be different kinds of cameras, such as CCD (Charged Coupled Device) cameras and CMOS (Complementary Metal Oxide Semiconductor) cameras.

Instead of using triangulation laser scanning, where a sheet of laser light is sent as in, a time-of-flight laser scanning technique may be used. In this technique, a pulsed point laser source sweeps over a portion of patient's body and sends laser light in the form of pulsed laser spots. For a 2D representation, the laser source sweeps along a determined contour line on the body, whereas for 3D representations the laser sweeps over one or several predetermined body surface(s). The detector detects the pulsed laser spots that are reflected off the body surface of the patient. Based on this detected data, using known imaging algorithms, a 2D or 3D surface representation of the patient surface is obtained.

A third possible laser scanning technique is an interference-based imaging process. In this technique, the laser beam from the laser source is split into two different beams, a first beam is directed onto the patient, where it is reflected and detected by the detector, whereas the second beam is directed onto the detector. In the detector, the patient is depicted as a pattern of light and dark interference bands. This technique has very high-resolution at the cost of complex imaging processing.

The data memory 120 is preferably also configured to store a reference surface representation of a least a portion of the surface of the patient 30. This reference surface representation can, for instance, constitute part of a treatment plan that has previously been generated for the particular patient 30. The reference surface representation can be recorded in connection with another medical machine, such as a diagnostic machine or during treatment stimulation. Alternatively, the reference surface representation is generated at the same machine but at a previous positioning occasion. In such a case, the reference surface representation is preferably a surface representation of at least a portion of the surface of the patient 30 generated by a pattern analyzing circuit 110 based on a detection signal from a detector 80, 85 arranged in connection with the (another) medical machine. Thus, in a preferred implementation, each medical machine that is employed in connection with providing diagnostic information, conducting treatment simulation and providing radiation therapy is preferably equipped with or has access to a respective pattern projector 70 and detector 80, 85 to allow generation of a surface representation of the patient 30 in connection with the medical machine 1.

It is actually possible to have a reference surface representation that is not recorded based on any pattern detection. In clear contrast, the reference surface representation can be a "virtually" or computer-generated surface representation. For instance a body or organ atlas is more and more commonly used within the field of diagnosis. The atlas is a database or data bank comprising anatomical information of the human body or a portion of it. Such an atlas may be developed from several different diagnostic measurements collected from different patients. In other words, the atlas is typically a representation of an average human, preferably containing all major organs and tissues, skeleton and nervous system. The reference surface representation could then correspond to a representation obtained from such an atlas, possibly following modification to adjust scale, etc. of the atlas body to correspond to the particular patient body 30.

A correction analyzing circuit 130 is configured to generate a correction signal based on the surface representation generated by the pattern analyzing circuit 110 and the reference surface representation from the data memory 120. The correction signal is representative of a discrepancy in at least one of position and posture of the surface representation relative the reference surface representation. Thus, the correction signal is indicative of how the patient 30 should be moved, such as translated and/or rotated, in order to reach a target position as defined by the reference surface representation. In addition or alternatively, the correction signal could be indicative of a discrepancy in posture of individual body parts relative a target posture for the patient 30 as defined by the reference surface representation.

The positioning system also comprises a light projector 70, 75 that is responsive to the correction signal from the correction analyzing circuit 130. The light projector 70, 75 projects information 55 representing the discrepancy in position and/or posture onto the patient 30 and/or onto a surface of the couch 20.

The projected information 55 therefore provides information of the current position and/or posture of the patient 30 relative the target position and/or posture. The projected information 55 can be regarded as defining instructions of how the patient 30 should be repositioned in order to reach the target position and/or posture. This means that the projected information 55 defines the discrepancy between current position and/or posture and the target position and/or posture.

In clear contrast to prior art solutions, the information 55 representing the discrepancy is projected directly onto the patient body 30 or optionally onto some other surface of the couch 20 to thereby be visually available for the medical personnel operating close to the couch 20 and the patient 30. This means that information 55 required in order to determine how the patient 30 should be repositioned is directly available to the personnel close to where they are standing.

In a preferred embodiment, the information 55 is projected onto the patient body 30 as schematically illustrated in FIG. 1. For instance, in the case of a human patient 30 the information 55 can be projected onto the stomach and/or chest of the patient 30 as these body portions provide a comparatively large and flat portion that is well suited for display of the information 55. If the patient instead would be lying on the stomach, the information 55 can advantageously be projected somewhere on the back of the patient 30. Projection of the information 55 onto the patient body 30 is in particular suitable in connection with information 55 representing a discrepancy in posture of the patient 30 relative a target posture, which is further described herein.

Instead of or as a complement to projecting the information 55 onto the patient surface, the light projector 70, 75 can be configured to project the information 55 onto a surface of the couch 20. In such a case, this surface is preferably a predefined surface part of the couch 20 that is visually accessible to the medical personnel when standing next to the patient 30 and the couch 20. The personnel can then look directly at this part of the couch 20 when repositioning the patient 30 instead of watching a remote display screen as in the prior art.

In a particular embodiment, the correction analyzing circuit 130 is configured to generate a correction signal representative of a rigid body translation of the surface representation to a target position as defined by the reference surface representation. Thus, in this embodiment the surface representation as determined by the pattern analyzing circuit 110 is employed to define a rigid-body representation of at least a portion of the patient 30. The coordinates of this rigid-body representation relative corresponding coordinates of a reference rigid-body representation as defined by the reference surface representation is then determined. Matching surface representations, such as rigid-body representations, are well known in the art and are for instance disclosed in the above mentioned Medical Image Analysis article.

The correction analyzing circuit 130 then generates the correction signal that is forwarded to the light projector 70, 75 for projecting information 55 defining a translation of the patient 30 to reach the target position. Such translation defining information 55 preferably relates to a translation of the patient 30 in a Cartesian coordinate system. For instance, a first axis of the coordinate system could correspond to a height adjustment of the patient 30 relative the target position. A second coordinate axis corresponds to a longitudinal adjustment of the patient 30 along the longitudinal or anteroposterior axis of the patient 30. The third and final coordinate axis corresponds to a lateral adjustment of the patient 30 along the lateral, transverse, latitudinal or left-right axis.

In a preferred embodiment, the couch 20 comprises a movable table top 25 onto which the patient 30 or other object to be repositioned is lying. The table top 25 can then be moved relative a base unit of the couch 20 along its longitudinal axis (corresponds to second coordinate axis according to above) or a transverse axis (corresponds to third coordinate axis according to above). Additionally, the height of the table top 25 relative the floor can advantageously be adjusted in the base unit.

In a first embodiment, the table top 25 can be manually operated by medical personnel, for instance, by pushing the table top along rails in the base unit. The information 55 projected onto the patient body 30 then provides instructions of how much the table top should be moved and in what directions (longitudinal, transverse and/or up/down) to get the patient 30 in the desired target position.

In an alternative embodiment, the couch 20 comprises a motor and motor control that operates the motor to thereby move the table top 25 relative the base unit along the longitudinal and/or transverse direction and/or adjust the height of the table top 25 and the patient 30 there on. The medical personnel will then be standing at the motor control that can be implemented in the form of a joystick, push buttons, or some other user input device 22, see FIGS. 7 and 8. At this position, typically close to the base unit of the couch 20, the medical personnel has visual access to the projected information that informs the personnel of how the table top 25 and patient 30 should be moved to get into the target position.

Figure 10:
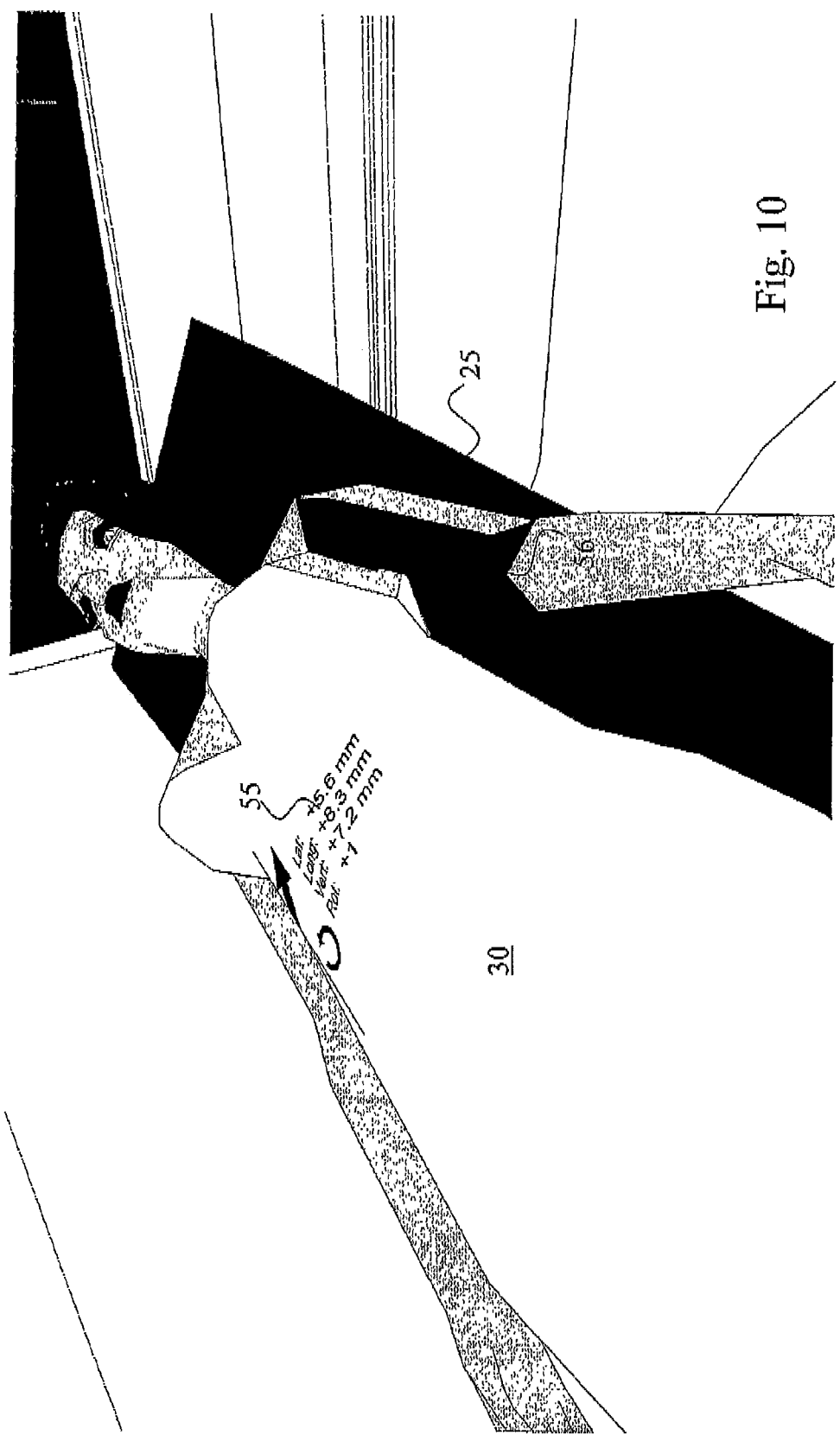
FIG. 10 illustrates the projection of discrepancy information according to an embodiment.
Figure 11:
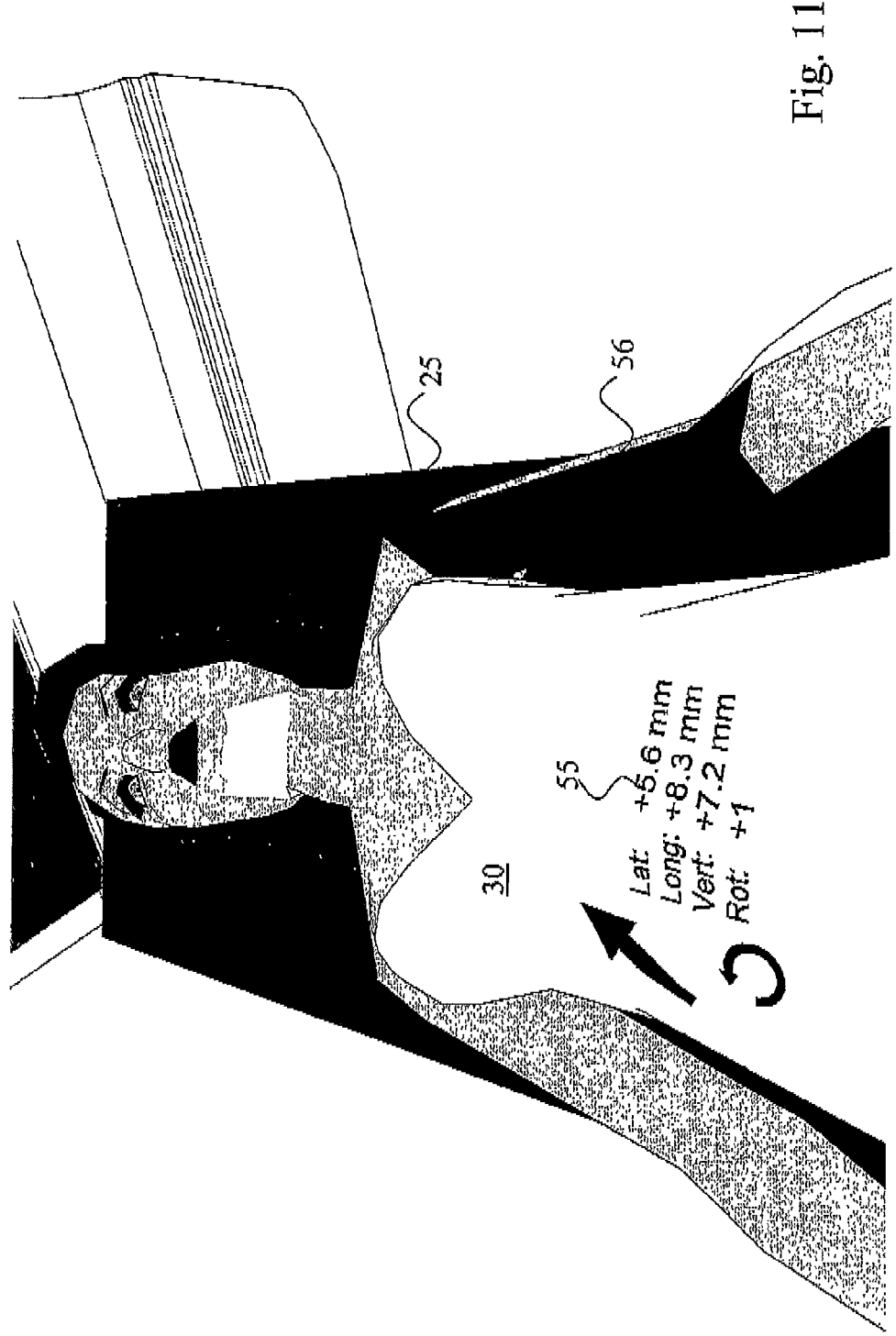
FIG. 11 illustrates the projection of the discrepancy information in FIG. 10 from another view.

FIGS. 10 and 11 illustrate an example of projected information 55 defining a translational movement of the patient. In this case, adjustment information 55 along the three coordinate axes is displayed onto the patient 30, here represented by a latitudinal adjustment of 5.6 mm, a longitudinal adjustment of 8.3 mm and a height or vertical adjustment of 7.2 mm. As is illustrated in the figure, the sign (plus versus minus) can be used to define the direction of the movement along respective axis. Additionally, or in addition, the projected information 55 can include an arrow that illustrates the direction of the adjustments that are needed in order to move the patient 30 from the current position and into the target position.

Instead of or preferably as a complement to translational adjustment, the projected information 55 can be generated based on a correction signal from the correction analyzing circuit 130 that is representative of a rigid body rotation of the determined surface representation and therefore the patient 30 to a target position as defined by the reference surface representation. The rotation can be around a dorsoventral axis of the patient, i.e. a vertical axis. Alternatively, the rotation of the patient can be around the anteroposterior axis of the patient, i.e. a horizontal axis. It is also possible that rotations relative both these rotation axes are needed in order to reach the target position. In such a case, the projected information 55 preferably comprises representation of both such rotation adjustments.

FIGS. 10 and 11 illustrate how such rotational information can be implemented by projecting information 55 defining a rotation of the patient 30 in terms of a rotation angle representation to reach the target position. In the figure, the patient 30 should be rotated 1° around the vertical axis. In similarity to the translational information, a sign can be used to define the rotation direction. Alternatively, or in addition, a graphical representation of the rotation direction can be displayed in the form of semi-circular arrow.

FIGS. 7 and 8 illustrate that the couch 20 can advantageously be connected to a rotating disk in the floor. The disk enables rotation of the couch 20 and the patient 30 around the central vertical axis of the disk.

In addition to generating and projecting the information 55 onto the patient based on the correction signal, the positioning system can optionally comprise a couch control circuit 140. This couch control circuit 140 generates a couch control signal based on the correction signal. The couch control signal controls the motor of the couch 20 to thereby cause an automatic movement of the table top 25 of the couch 20 according to the couch control signal. Thus, in this embodiment, the displayed information 55 can mainly be for information purposes since the position adjustment is conducted automatically based on the couch control signal. However, in practical applications the type of automatic movement that can be achieved through a couch control signal is somewhat limited. This means that the couch control signal can be used to perform an automatic, rough adjustment of the patient position. The medical personnel then conduct the remaining fine adjustment of the patient position based on the projected information 55 and using the user input device 22.

The rigid-body adjustment information 55 that can be projected onto the patient 30 or couch surface can comprise numerical values, graphical information or a combination thereof as illustrated in FIGS. 10 and 11. This provides a visually appealing and informative data display that can easily be interpreted by the medical personnel.

The positioning system can also be implemented with a correction analyzing circuit 130 configured to generate a correction signal representative of a posture deformation of the patient 30 relative a target posture defined by the reference surface representation. The advantage of such posture deformation in contrary to rigid-body adjustments is that the posture of individual body parts can be corrected. For instance, a patient 30 present in a target position as defined based on rigid-body representations can still have a target volume 35 inside the body 30 that is somewhat misaligned with a desired position according to a treatment plan due to posture misalignments. If, for example, the left shoulder of the patient 30 is positioned too low as compared to a target posture, a resulting local rotation of the upper torso can cause a slight movement of the target volume 35 as compared to the situation when the shoulder is lifted slightly to prevent the rotation of the upper torso. Such local posture misalignments of different body parts can generally not be detected or combated through rigid-body representations. The positioning system consequently advantageously in addition or alternatively also handles posture deformations and preferably posture deformations of individual body parts of the patient 30 relative a target posture.

The light projector 70, 75 is consequently in this embodiment configured to project information 56 defining a posture deformation of onto the patient 30 or the couch surface. In a preferred embodiment, the information 56 defining the posture deformation is preferably projected onto the individual body part that is misaligned as determined based on the surface representation and the reference surface representation. This means that the light projector 70, 75 projects the information 56 of posture deformation directly onto the part of the patient 30 that needs to have its posture deformed to reach the target posture. Such an information projection will be highly informative and easy to interpret to thereby correctly identify how the posture of the patient 30 should be changed.

The information 56 relating to posture deformation can advantageously be in the form of graphical information 56 as illustrated in FIGS. 10 and 11. In this example, a light pattern 56 is projected onto the body part (upper left arm) that needs to be moved slightly to reach the target posture. A first embodiment can include a light projector 70, 75 that merely projects a light pattern 56 onto the relevant body part. In a more elaborate embodiment, the projected light pattern 56 can additionally carry further information by defining how the posture deformation should be conducted. For instance, the projected light pattern 56 can be of different colors to indicate how close the current posture of the body part is to the target posture. As an example, a red color could indicate a comparatively large difference between current and target posture, yellow signals a slight difference whereas green light indicates that the target posture has been reached. In a further embodiment, the color of the projected pattern 56 not only indicates how far the current posture is from the target posture but also how the body part should be moved to reach the target posture. For instance, red could indicate a relative large upward movement of the body part, yellow indicate a small upward movement, blue indicate a small downward movement of the body part and purple indicate a relatively large downward movement of the body part. Instead of or as a complement to such graphical information, the projected information 56 could include numerical and/or text data to indicate for the medical personnel how the individual body part should be moved to reach its target posture.

In a preferred embodiment, the positioning system can generate and project information 55, 56 representative of both discrepancy in patient position and posture, which is illustrated in FIGS. 10 and 11. This means that any misalignments in terms of translational, rotational and posture misalignment can be determined and combated using the projected information 55, 56.

The positioning system can be configured to perform a single surface representation determination of the patient 30 and generate the information 55, 56 that is projected onto the patient 30 once, for instance in connection with patient set-up. However, it is generally preferred if updated surface representation determinations of the patient 30 are performed to thereby generate updated information 55, 56 that can be projected onto the patient 30. In such a case, the medical personnel can use the initially projected information 55, 56 to reposition the patient according to the information 55, 56. Thereafter the pattern projector 70 projects once more a 2D or 3D pattern that is detected by the detector 80, 85 to generate updated detection signal. The pattern analyzing circuit 110 processes the updated detection signal to generate an updated surface representation that is compared by the correction analyzing circuit 130 to the reference surface representation. An updated correction signal representative of the current discrepancy in position and/or posture of the determined surface representation relative the reference surface representation is generated by the correction analyzing circuit 130 and employed for projecting updated information 55, 56 by the light projector 70, 75.

The medical personnel can then check whether any further patient repositions are needed or if the target position has been reached. In this embodiment, the positioning system is activated to perform a position/posture information update based on activation of a user input by the medical personnel. This means that a user has to trigger activation of the positioning system. In an alternative embodiment, the positioning system can be continuously or periodically active during a measurement session. This means that the positioning system in real-time or close to real-time determines the current patient position and posture and the discrepancy relative the target position and posture. In order to achieve a real-time, continuous measurement of the surface the sampling frequency of the positioning system is preferably in the sub-second range. However, in most practical near real-time applications, the sampling to determine an updated surface representation and updated discrepancy information 55, 56 could be conducted from every other second up to every 30 second.

The pattern projector 70 of the positioning system is preferably configured to project the 2D or 3D pattern in the form of passive structured light or active structured light. For instance, structured light in the form of projecting a narrow 2D band of light 40 onto the surface of the object 30 produces a line of illumination that appears distorted from other perspectives than that of the pattern projector 70. Thus, by positioning the detector(s) 80, 85 at spatially different positions relative the pattern projector 70 the detected distorted illumination line can be used for an exact geometrical reconstruction of the surface shape. In order to cover a larger portion of the object surface, the pattern projector 70 can project this band of light 40 onto different surface portions for instance by traveling the line over the surface. At each position of the line the detector(s) 80, 85 register the illuminated line of the surface to thereby allow determination of a 3D surface representation.

Figure 5:
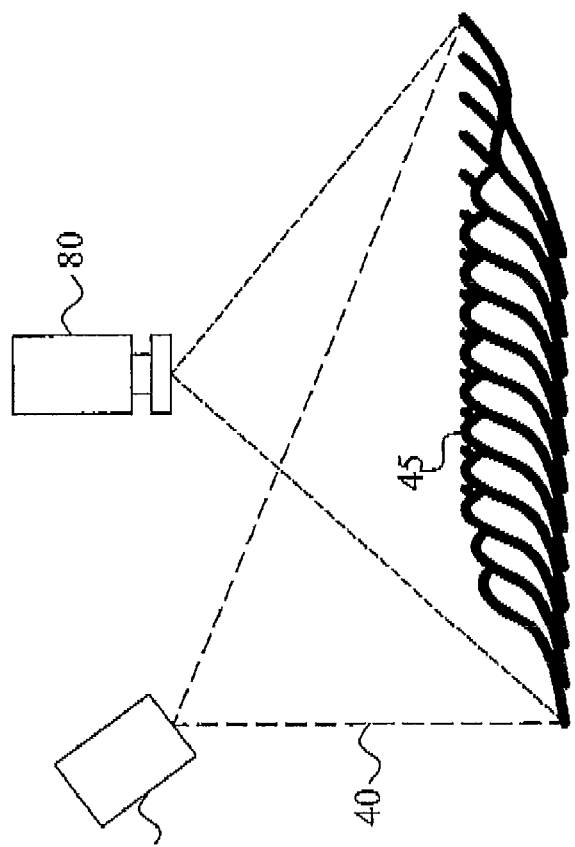
FIG. 5 schematically illustrates projecting structured light for the purpose of determining a 3-dimensional surface representation.

A faster and more versatile method is not to project a 2D pattern (band) but instead a 3D pattern consisting of many stripes 45 at once or of arbitrary fringes, which is schematically illustrated in FIG. 5. In the figure the pattern projector 70 projects a light beam 40 with the desired pattern 45 onto the surface, and the resulting distorted pattern is registered by the detector 80.

The projected light structures can be regular ones, such as cross patterns, circles e.g., speckled or random, or striped patterns. Generally, pattern features perpendicular to the projector/camera baseline will contribute a lot more triangulation hints than features parallel to it. Hence, stripe patterns in this perpendicular direction are preferred. For the main task of accurate coordinate acquisition, stripe patterns with (in the ideal case) cosine shaped brightness (cost intensity) gradients are suitable. By exploiting intensity gradients, triangulation is made independent of the actual pixel raster and distances can be measured at very high resolution.

A positioning system based on striped pattern projection 70 in principle needs just one detector 80, such as camera, and one pattern projector 70. Key parameters are object distance, field of view and the angle between camera and projector, defining the triangulation base. For full parts digitization, requiring views from many angles, two detectors as illustrated in FIGS. 2 and 3 preferably positioned on either side of the pattern projector 70 can be used. Placed on both sides of the central pattern projector 70, these cameras 80, 85 deliver two pictures at a time, thereby speeding up the process, as well as avoiding possible asymmetric properties of a one detector. Additionally, usage of multiple, i.e. at least two, detectors 80, 85, also allow for full or partly photogrammetric operation (principle of a stereo camera but with artificial features inserted into bald surfaces).

The positioning system can have a dedicated pattern projector 70 and a dedicated light projector 75 as illustrated in FIG. 3. Alternatively, the same projector 70 can operate both as pattern projector and light projector, which is schematically illustrated in FIG. 2. Regardless of implementation choice, the pattern projector 70 or common projector preferably projects the 2D or 3D pattern 45 as a light pattern of a first wavelength or wavelength interval. The light projector 75 or common projector then projects the information 55, 56 as visible light in a second wavelength of a second wavelength interval that is different from the first wavelength or first wavelength interval. For instance, the light projector 70, 75 can project a beam of visible light 50 onto the patient within the visible spectrum, i.e. from about 380 to 750 nm. A single wavelength or a narrow wavelength interval within the visible spectrum could be employed, though it can be preferred to utilize different color and therefore different wavelengths for the projected information 55, 56 as previously described.

The pattern projector 70 is then preferably configured to project the 2D or 3D pattern as a beam 40 of non-visible light. For instance, ultraviolet (UV) light in the range of about 10 to 400 nm or IR light in the range of about 700 to 3,000 nm can be used by the pattern projector 70.

The at least one detector 80, 85 preferably comprises a band-pass filter configured to pass light 40 projected by the pattern projector 70, i.e. in the first wavelength interval, but attenuate light 50 projected by the light projector 70, 75, i.e. in the second wavelength interval. This solution is in particular advantageous in connection with continuous or near-continuous surface measurements since then both the pattern projector 70 and the light projector 70, 75 can be active simultaneously and the detector(s) 80, 85 do(es) not have to be switched off during the projection of the information 55, 56 by the light projector 70, 75.

A preferred implementation of a common projector for both the pattern projector and the light projector is to employ a digital light processing (DLP) projector. A DLP projector employs moving micro mirrors and a DLP chip onto which the light is displayed. The DLP chip does not absorb light significantly and therefore allow very high light intensities. It also has an extremely linear gray value reproduction as it is steered by pulse length modulation. Such a DLP projector can advantageously be used in connection with structured light as 2D or 3D pattern.

Figure 6:
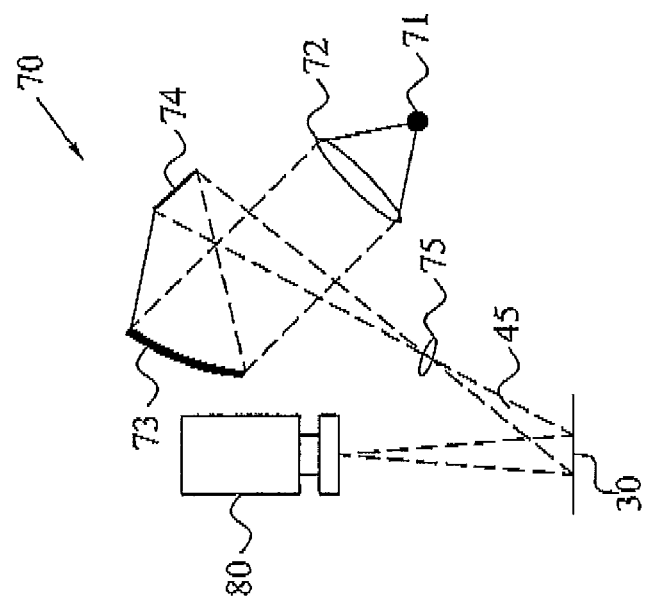
FIG. 6 schematically illustrates the principles behind digital light projection that can be used according to embodiments.

FIG. 6 illustrates an implementation of a DLP projector 70 using a light-emitting diode (LED) 71 as light source. It is actually not as flat as depicted, as the micro mirrors are tilting diagonally. A condenser lens 72 and a slightly concave mirror 73 are guiding the light towards the DLP chip 74. The DLP chip 74 comprises microscopically small mirrors laid out in a matrix of a semiconductor chip or substrate, generally known as Digital Micromirror Device (DMD). Each mirror represents one or more pixels in the projected pattern. The reflected light from the mirrors passes through a projector lens 75 to direct the light 45 onto the surface of the patient 30, where it is detected by the detector 80.

In order to provide both light to be employed for the 2D or 3D pattern and the light of the discrepancy information, a LED or other light source 71 that capable of providing light of different wavelengths can be used. Alternatively, a color wheel can be placed between the light source 71 and the DLP chip 74 to switch between different colors. In yet another approach multiple individual light sources 71 can be used to produce the different colors or light types (visible vs. UV or IR). The light sources 71 can be LEDs or lasers for example. It is also possible to use a so called three-chip DLP projector having a prism to split light from a light source 71 and direct each split light beam to its own DLP chip and then recombine and rout the light through the projector lens 75.

The detectors 80, 85 employed in connection with a pattern projector 70 configured for usage with digital fringe projection preferably has a camera resolution at least as good as the pattern projector 70. There is no restriction towards higher resolutions however, as by the fact of the continuous gray level gradients used, detector and projector resolution and even so height resolution are largely independent of each other. A higher detector resolution mainly adds to the lateral resolution of the positioning system, important in many applications, but also increases noise and reduces depth of filed. The detector 80, 85 can advantageously be implemented in the form of a camera, such as the MikroCAD by GFM.

The pattern projector 70 and the detector(s) 80, 85 are preferably arranged together on a common rack or structure 60 as illustrated in FIGS. 2 and 3. If a separate light projector 75 is used in the positioning system, it can also advantageously be arranged in the rack 60, which is schematically depicted in FIG. 3. The rack 60 is preferably designed to be attached to a ceiling in the room in which the positioning system is operable. This is illustrated in FIGS. 1, 7-9. Such an arrangement of the projectors 70, 75 and detectors 80, 85 enables comparatively large viewing angles to thereby be able to capture the whole surface of the patient 30 if desired. The large viewing angle implies that the risk of body parts shadowing other body surface parts is reduced to thereby have a constant field of view by the detectors 80, 85 of the relevant patient surface.

The pattern analyzing circuit 110, the correction analyzing circuit 130 and the optional couch control circuit 140 can be implemented in a common data processing unit 100 preferably together with the data memory 120 as illustrated in FIG. 4. The data processing unit 100 can be implemented as a computer or other data processing unit that is connected to the detector(s) of the positioning system and preferably to the projectors 70, 75 for the purpose of controlling these.

If the positioning system is employed in connection with non-living objects, such as fixation equipment, these units can advantageously each comprise a visually detectable identification label. For instance, each object can have a dedicated bar code. These bar codes or other identification label are preferably arranged on the objects so that the bar codes can be read or captured by the detector 80, 85, in particular if camera-based detectors 80, 85 are employed. In such a case, the data processing unit 100 preferably comprises an object identifier 150 that processes the captured image of the bar code for the purpose of identifying the particular object. The memory 120 of the data processing unit 100 or a remote memory, though accessible for the data processing unit 100 can then include information of different objects and their respective bar codes or identification labels. For instance, the memory 120 can store reference surface representations generated for multiple different objects. The particular reference surface representation that should be used for a particular object can then be automatically selected by the pattern analyzing circuit 110 or a dedicated representation identifier (not illustrated in FIG. 4) of the data processing unit 110 based on the output of the object identifier. Thus, each reference surface representation stored in the memory 120 is associated with an identifier of the relevant object and the stored identifiers are compared by the object identifier with the bar code or identification label captured by the detector 80, 85.

The data processing unit 100 is preferably connectable to a user input 160, such as a touch sensitive screen, keyboard or mouse, which allows a user to enter data to the data processing unit 100. Such entered data could be an identifier of an animal or human object to be positioned based on the positioning system. For instance, the social security number, personal code number of the patient 30 or a local identifier assigned to the patient 30 at the healthcare facility could be such identifier. In such case, the memory 120 could store reference surface representations associated with multiple different patients 30. The pattern analyzing unit 110 of the data processing unit 100 then receives the identifier from the user input 160 and employs the identifier for identifying and fetching the relevant reference surface representation from the memory 120.

The memory 120 or some other memory connected to the data processing unit 100 can additionally store other patient relevant information, such as personal specific data, including patient name, social security number or other identifier according to above, the treatment plan, etc. This patient information can also be of interest for the medical personnel. In such a case, the light projector 70, 75 not only projects the information representing the discrepancy in patient position and/or posture but also the patient information. For instance, the memory 120 can store name and a photo of the patient 30. Once the medical personnel has entered an identifier of the patient 30 in the user input 160, the relevant patient information of the patient can be automatically retrieved from the memory 120 by the data processing unit 100. The retrieved patient information is forwarded to the light projector 70, 75 for projection onto the patient 30 or the couch surface. There the medical personnel can verify that the patient information relates to correct patient 30 by checking the projected social security number or photo. If it correct, the medical personnel will know that the reference surface representation that is also retrieved from the memory 120 based on the input identifier will correspond to the correct patient 30.

Thus, the positioning system and its light projector 70, 75 does not have to only project information relating to patient position and/or posture but could additionally project all information that is of relevance for the medical personnel. For instance, the treatment plan of the patient 30 could specify that a cushion should be placed beneath the patient's knees. This information fetched from the memory 120 can be projected onto the patient 30 to thereby inform the medical personnel of this additional or side information that is relevant to the patient 30 and the treatment.

The pattern analyzing circuit 110, correction analyzing circuit 130, the couch control circuit 140, object identifier 150 and user input 160 can be implemented by a programmable microcontroller of the data processing unit 100 that controls the operation of the positioning system. The controller then typically includes a microprocessor, or equivalent control circuitry, designed specifically for effectuating the operation of these circuits 110, 130, 140, 150, 160, and may further include RAM or ROM memory, logic and timing circuitry, state machine circuitry, and input/output (I/O) circuitry.

The circuits 110, 130, 140, 150, 160 of the data processing unit 100 may be implemented or provided as software, hardware or a combination thereof. In the case of a software-based implementation, a computer program product implementing the circuits 110, 130, 140, 150 or a part thereof comprises software or a computer program run on a general purpose or specially adapted computer, processor or microprocessor. The software includes computer program code elements or software code portions illustrated in FIG. 4. The program may be stored in whole or part, on or in one or more suitable computer readable media or data storage means such as magnetic disks, CD-ROMs, DVD disks, USB memories, hard discs, magneto-optical memory, in RAM or volatile memory, in ROM or flash memory, as firmware, or on a data server.

It is known in the art that different markers can be attached to the patient for facilitating correct positioning, such as IR markers as discussed in the background section. Such marker can of course be illuminated by the pattern projector 70 and detected by the detector 80, 85 of the positioning system. However, an advantage of the embodiments is that no such markers are needed in order to achieve an efficient patient positioning by the positioning system.

Figure 12:
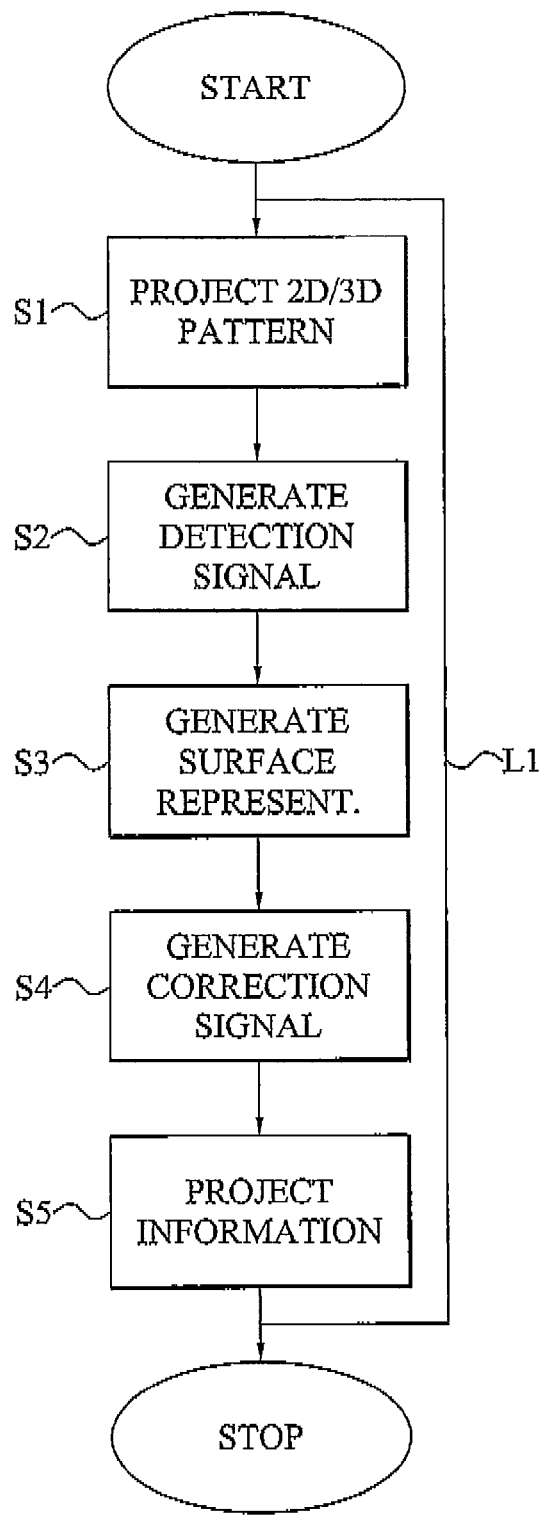
FIG. 12 is a flow diagram illustrating an object positioning method according to an embodiment.

FIG. 12 is a flow diagram illustrating an object positioning method according to an embodiment. The method starts in step S1 where a 2D or 3D pattern is projected onto a surface of an object positioned on a couch. The projected pattern is detected and a detection signal representative of the detected 2D or 3D pattern on the object surface is generated in step S2. The detection signal is processed in step S3 for the purpose of generating a surface representation of at least a portion of the object surface based on the detection signal. The surface representation is compared to a reference surface representation, preferably by comparing the coordinates of points on the surface representation with the coordinates of corresponding or matching points on the reference surface representation. A correction signal representative of a discrepancy in position and/or posture of the surface representation and the reference surface representation is generated in step S4 based on the comparison. Information representing this detected discrepancy in position and/or posture is projected onto the object surface or onto some other surface portion of the couch to there become visible to personnel operating close to the couch and object.

As has previously been discussed updated detection signals, surface representations, correction signals and projected information are preferably generated either semi-continuously, periodically or upon user-activation to thereby allow the personnel to get visibly projected updated information of the current discrepancy of the object position and/or posture as it is being repositioned or following a reposition. This is schematically illustrated by the line L1 in the figure.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A positioning system comprising:
   a pattern projector configured to project a 2- or 3-dimensional pattern onto a surface of an object positioned on a couch;
   a detector responsive to said projected 2- or 3-dimensional pattern and configured to generate a detection signal representative of a detected 2- or 3-dimensional pattern on said surface of said object;
   a pattern analyzing circuit connected to said detector and configured to generate a surface representation of at least a portion of said surface of said object based on said detection signal;
   a memory configured to store a reference surface representation of at least a portion of said surface of said object;
   a correction analyzing circuit configured to generate a correction signal representative of a discrepancy in at least one of position and posture of said surface representation relative said reference surface representation; and
   a light projector connected to said correction analyzing circuit and configured to project information representing said discrepancy in at least one of position and posture onto said object or a surface of said couch.

2. The positioning system according to claim 1, wherein said correction analyzing circuit is configured to generate a correction signal representative of a rigid body translation of said surface representation to a target position as defined by said reference surface representation.

3. The positioning system according to claim 2, wherein said light projector is configured to project information defining a translation of said object to reach said target position.

4. The positioning system according to claim 3, wherein said light projector is configured to project information defining said translation in a Cartesian coordinate system, where a first coordinate axis corresponds to height adjustment of a table top of said couch, a second coordinate axis corresponds to longitudinal movement of said table top and a third coordinate axis corresponds to transverse movement of said table top, said table top is designed to carry said object.

5. The positioning system according to claim 1, wherein said correction analyzing circuit is configured to generate a correction signal representative of a rigid body rotation of said surface representation to a target position as defined by said reference surface representation.

6. The positioning system according to claim 5, wherein said light projector is configured to project information defining a rotation of said object in terms of a rotation angle representation to reach said target position.

7. The positioning system according to claim 1, wherein said correction analyzing circuit is configured to generate a correction signal representative of a posture deformation of said object relative a target posture defined by said reference surface representation.

8. The positioning system according to claim 7, wherein said correction analyzing circuit is configured to generate a correction signal representative of a posture deformation of an individual body part of said object relative said target posture.

9. The positioning system according to claim 8, wherein said light projector is configured to project information defining a posture deformation of said individual body part relative said target posture onto said body part.

10. The positioning system according to claim 1, wherein said detector comprises a first detector and a second spatially separated detector.

11. The positioning system according to claim 1, wherein said pattern projector and said detector are arranged on a rack designed to be attached to a ceiling.

12. The positioning system according to claim 1, wherein said pattern projector is configured to project a 2- or 3-dimensional non-visible light pattern.

13. The positioning system according to claim 1, wherein said pattern projector and said light projector is a same projector configured to project a 2- or 3-dimensional light pattern of a first wavelength interval and project said information by visible light in a second wavelength interval different from said first wavelength interval.

14. The positioning system according to claim 13, wherein said detector comprises a band-pass filter configured to pass light of said first wavelength interval but attenuate light of said second wavelength interval.

15. The positioning system according to claim 13, wherein said same projector is a digital light processing, DLP, projector.

16. The positioning system according to claim 1, further comprising a couch control circuit configured to generate, based on said correction signal, a couch control signal to cause an automatic movement of a table top of said couch according to said couch control signal, said table top is configured to carry said object.

17. An object positioning method comprising:
projecting a 2- or 3-dimensional pattern onto a surface of an object positioned on a couch;
generating a detection signal representative of a detected 2- or 3-dimensional pattern on said surface of said object;
generating a surface representation of at least a portion of said surface of said object based on said detection signal;
generating a correction signal representative of a discrepancy in at least one of position and posture of said surface representation relative a reference surface representation of at least a portion of said surface of said object stored in a memory; and
projecting information representing said discrepancy in at least one of position and posture onto said object or a surface of said couch.

18. The method according to claim 17, wherein generating said correction signal comprises generating a correction signal representative of a rigid body translation of said surface representation to a target position as defined by said reference surface representation.

19. The method according to claim 17, wherein generating said correction signal comprises generating a correction signal representative of a rigid body rotation of said surface representation to a target position as defined by said reference surface representation.

20. The method according to claim 17, wherein generating said correction signal comprises generating a correction signal representative of a posture deformation of said object relative a target posture defined by said reference surface representation.

21. The method according to claim 20, wherein
generating said correction signal comprises generating a correction signal representative of a posture deformation of an individual body part of said object relative said target posture; and
projecting information comprises projecting information defining a posture deformation of said individual body part relative said target posture onto said body part.

22. The method according to claim 17, wherein projecting said 2- or 3-dimensional pattern comprises projecting a 2- or 3-dimensional non-visible light pattern.

23. The method according to claim 17, wherein projecting said 2- or 3-dimensional pattern comprises projecting a 2- or 3-dimensional light pattern of a first wavelength interval and project said information comprises projecting said information by visible light in a second wavelength interval different from said first wavelength interval.

24. The method according to claim 23, further comprising band-pass filtering said detected 2- or 3-dimensional pattern to pass light of said first wavelength interval but attenuate light of said second wavelength interval.

25. The method according to claim 17, further comprising generating, based on said correction signal, a couch control signal to cause an automatic movement of a table top of said couch according to said couch control signal, said table top is configured to carry said object.

* * * * *